(12) United States Patent  (10) Patent No.: US 9,239,280 B2
Kulkarni  (45) Date of Patent: Jan. 19, 2016

(54) MEASUREMENT OF SERUM LIPOPROTEINS

(71) Applicant: ATHEROTECH, INC., Birmingham, AL (US)

(72) Inventor: Krishnaji R Kulkarni, Vestavia, AL (US)

(73) Assignee: ATHEROTECH, INC., Birmingham, AL (US)

( * ) Notice: Subject to any disclaimer, the term of this patent is extended or adjusted under 35 U.S.C. 154(b) by 0 days.

(21) Appl. No.: 13/842,577

(22) Filed: Mar. 15, 2013

(65) Prior Publication Data

US 2014/0049775 A1 Feb. 20, 2014

Related U.S. Application Data

(60) Provisional application No. 61/660,710, filed on Jun. 16, 2012.

(51) Int. Cl.
*G01N 15/06* (2006.01)

(52) U.S. Cl.
CPC .................................. *G01N 15/06* (2013.01)

(58) Field of Classification Search
USPC .............. 356/335–343, 36–41, 317–318; 435/287.2, 11; 436/71, 63, 164, 165, 436/171
See application file for complete search history.

(56) References Cited

U.S. PATENT DOCUMENTS

| 4,987,085 | A | * | 1/1991 | Allen et al. | 436/169 |
|---|---|---|---|---|---|
| 5,441,053 | A | * | 8/1995 | Lodder et al. | 600/473 |
| 5,460,974 | A | * | 10/1995 | Kozak et al. | 436/71 |
| 5,633,168 | A | | 5/1997 | Glasscock et al. | |
| 5,766,552 | A | * | 6/1998 | Doshi et al. | 422/535 |
| 5,928,484 | A | * | 7/1999 | Bellon et al. | 204/469 |
| 6,737,275 | B2 | * | 5/2004 | Purdie et al. | 436/71 |
| 7,521,248 | B2 | | 4/2009 | Kulkarni | |
| 7,700,360 | B2 | * | 4/2010 | Everhart et al. | 436/71 |
| 7,856,323 | B2 | | 12/2010 | Troup | |
| 2003/0136680 | A1 | * | 7/2003 | Benner et al. | 204/549 |
| 2004/0203070 | A1 | * | 10/2004 | Sovolainen et al. | 435/7.1 |
| 2005/0233439 | A1 | * | 10/2005 | Everhart et al. | 435/287.2 |
| 2008/0038762 | A1 | * | 2/2008 | Troup | 435/11 |
| 2008/0038763 | A1 | * | 2/2008 | Troup | 435/11 |
| 2008/0121025 | A1 | * | 5/2008 | Okazaki | 73/61.52 |
| 2010/0267631 | A1 | * | 10/2010 | Dasseux et al. | 514/7.4 |
| 2012/0315706 | A1 | * | 12/2012 | Caulfield et al. | 436/501 |

FOREIGN PATENT DOCUMENTS

JP        2002243745 A  *  8/2002

OTHER PUBLICATIONS

Kulkarni, et al. "Quanitifcation of cholesterol in all lipoprotein classes by the VAP-II method" 1994; Journal of Lipid Research, vol. 35, pp. 159-168.

* cited by examiner

*Primary Examiner* — Sang Nguyen
(74) *Attorney, Agent, or Firm* — Thomas G. Peterson; Bradley Arant Boult Cummings LLP

(57) ABSTRACT

Although a more accurate estimate of a person's risk of cardiovascular disease can be made on the basis of the number of lipoprotein particles per unit volume in the person's blood, current methods all rely on measuring the mass of lipoprotein cholesterol per unit volume. It has been discovered that a rapid and accurate lipoprotein particle count can be obtained by photometry. A method and apparatus are provided for measuring the number of lipoprotein particles in a sample using photometry.

9 Claims, 12 Drawing Sheets

MEASUREMENT OF SERUM LIPOPROTEINS

This application claims the benefit of U.S. Provisional Application No. 61/660,710, filed Jun. 16, 2012.

BACKGROUND

The measurement of blood lipoproteins is critical in predicting an individual's risk of many chronic diseases, particularly cardiovascular disease. Previously methods of measuring serum lipoproteins were only capable of determining the concentration of the lipoproteins in terms of mass of lipoprotein cholesterol per volume of serum. It has been discovered that a much more accurate predictor of cardiovascular disease is the number of lipoprotein particles per unit volume of blood (referred to herein as the "particle count"). However, at present there is no practical method of obtaining the particle count of lipoproteins that is suitable for use in the clinical setting. Lipoprotein particle counts are currently obtained using nuclear magnetic resonance techniques, but this approach is extremely expensive, of limited availability, and is not effective to enumerate certain lipoproteins, such as lipoprotein A. As a result it is not suitable for mass screening of patient populations.

Consequently, there is a long-felt but unmet need in the art for a method of enumerating serum lipoprotein particles, but which can be performed inexpensively in the clinical context, and which has the ability to enumerate particles of all significant types of lipoprotein.

SUMMARY

The following presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

The disclosure provides methods and apparatuses for enumerating lipoprotein particles in blood serum photometrically. It has been unexpectedly discovered that photometric measurements of lipoproteins in blood serum provide a rapid, inexpensive, and accurate count of lipoprotein particles. It has also been discovered that photometric measurement can be used effectively to count lipoprotein particles in particular lipoprotein fractions after relatively incomplete separation of the fractions, such as by density-gradient centrifugation. Light scattering measurements have been found to strongly correlate with lipoprotein particle count and to be robust in the presence of interfering serum components.

A general embodiment of the method comprises obtaining a photometric measurement of a serum lipid fraction from a subject; and calculating a particle count for the lipid fraction that is a function of the photometric measurement.

Another general embodiment of the method comprises separating a first serum lipid fraction in a sample; obtaining a measurement of light scattering in the first lipid fraction; and calculating a particle count for the first lipid fraction that is a function of the measurement of light scattering.

A more particular embodiment of the method comprises separating at least an HDL fraction, an LDL fraction, and a VLDL fraction in a sample; obtaining a measurement of the light scattering from at least one of the fractions; and calculating a particle count for each of the fractions from which a light scattering measurement was obtained, wherein the particle count is a function of the measurement of light scattering.

The method may further comprise separating additional fractions in addition to an HDL fraction, a lipoprotein A (LpA) fraction, an LDL fraction, and a VLDL fraction in a sample; obtaining a measurement of the light scattering from at least one of the fractions; and calculating a particle count for each of the fractions from which a light scattering measurement was obtained, wherein the particle count is a function of the measurement of light scattering.

In one embodiment, the method comprises separating at least an HDL fraction, a lipoprotein A (LpA) fraction, an LDL fraction, and a VLDL fraction in a sample; obtaining a measurement of the light scattering from at least one of the fractions; and calculating a particle count for each of the fractions from which a light scattering measurement was obtained, wherein the particle count is a function of the measurement of light scattering.

In one embodiment, the method comprises separating at least an HDL fraction, a lipoprotein A (LpA) fraction, an LDL fraction, an intermediate density lipoprotein (IDL) fraction and a VLDL fraction in a sample; obtaining a measurement of the light scattering from at least one of the fractions; and calculating a particle count for each of the fractions from which a light scattering measurement was obtained, wherein the particle count is a function of the measurement of light scattering.

In one aspect of the foregoing methods, a particle count is obtained for the LDL fraction. In one aspect of the foregoing methods, a particle count is obtained for the LDL fraction and at least one additional fraction. In one aspect of the foregoing methods, a particle count is obtained for the VLDL fraction. In one aspect of the foregoing methods, a particle count is obtained for the IDL fraction. In one aspect of the foregoing methods, a particle count is obtained for the LpA fraction.

An apparatus for obtaining a lipoprotein particle count from a sample is provided. A general embodiment of the apparatus comprises means for containing a liquid sample having vertically stratified fractions; means for conveying the lowest stratified fraction from the containing means; and means for counting particles configured to receive the lowest stratified fraction from the containing means by way of the conveying means. Another general embodiment of the apparatus comprises a sample vessel containing the sample; a liquid conduit positioned to collect the sample from the bottom of the sample vessel; and a light scattering counter positioned to receive the sample from the conduit.

Also provided is a method of calibrating the measurement of particle count of an atherogenic lipoprotein comprising obtaining a photometric measurement of an atherogenic lipoprotein from a calibration sample, measuring the molar concentration of apolipoprotein B100 (apoB) in the calibration sample, and calculating a regression between the photometric measurement and the molar concentration of apoB.

DETAILED DESCRIPTION

A. Definitions

Figure 1:
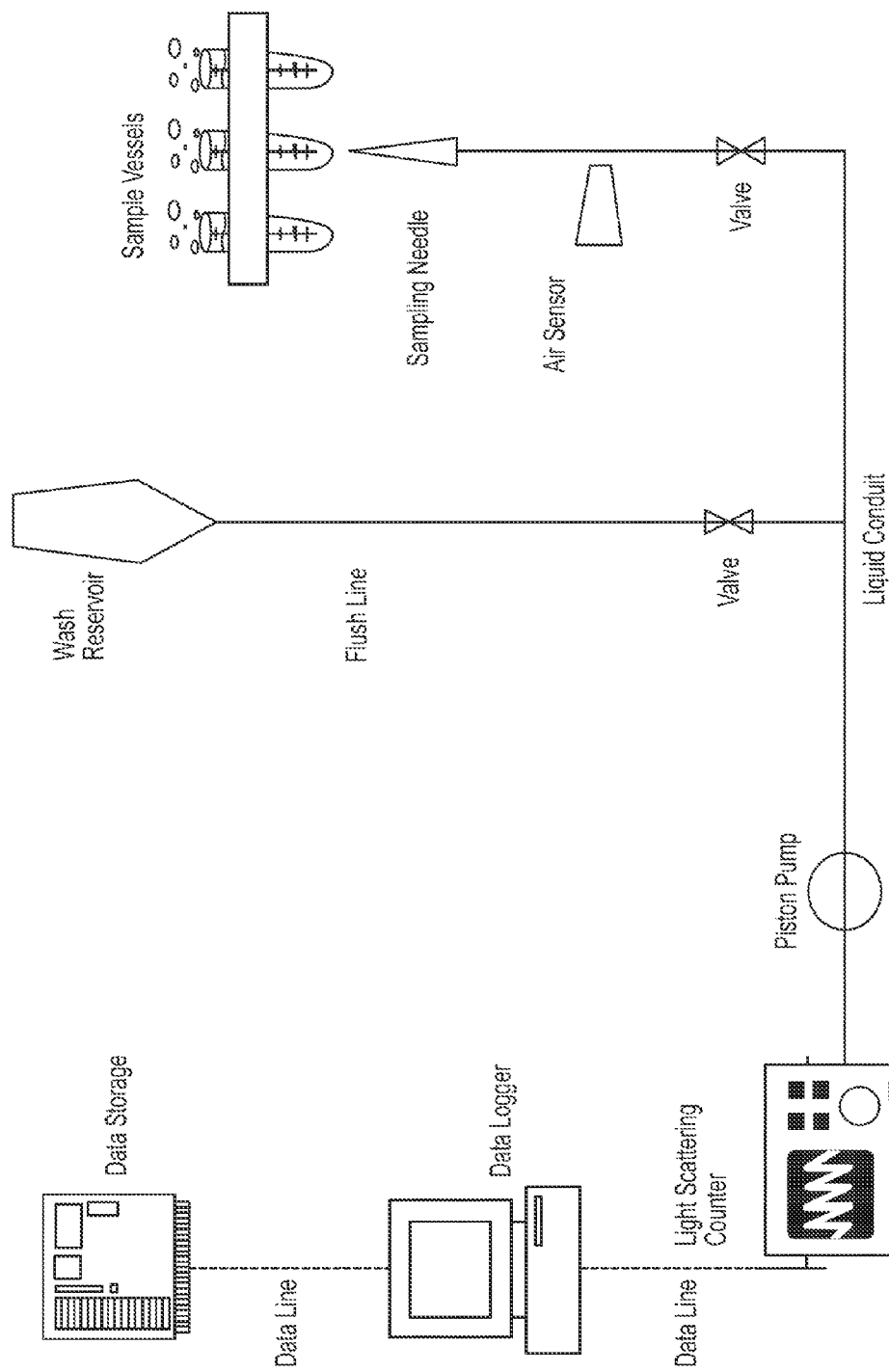
FIG. 1: A schematic illustration of an embodiment of the apparatus.

With reference to the use of the word(s) "comprise" or "comprises" or "comprising" in the foregoing description and/or in the following claims, unless the context requires otherwise, those words are used on the basis and clear understanding that they are to be interpreted inclusively, rather than exclusively, and that each of those words is to be so interpreted in construing the foregoing description and/or the following claims.

The term "individual", "subject" or "patient" as used herein refers to any animal, including mammals, such as mice, rats, other rodents, rabbits, dogs, cats, swine, cattle, sheep, horses, or primates, and humans. The term may specify male or female or both, or exclude male or female.

The term "about" as used herein refers to a value that is within a range around a central value, the range being a margin of error that would be expected by one of ordinary skill in the art based on accepted methods of measurement of the particular central value.

The terms "approximate" and "approximately" as used herein refer to a difference between an actual relationship between two variables and a calculated regression between the two variables that is relatively minor. For example, such a relationship with a variance above 0.5 or below −0.5 could be said to approximate the calculated regression.

B. Methods of Measuring Lipoproteins

Methods of measuring lipoprotein particle number in a sample from a subject are provided. A general embodiment of the method comprises obtaining a photometric measurement of a serum lipid fraction from a subject; and calculating a particle count for the lipid fraction that is a function of the photometric measurement.

Another general embodiment of the method comprises separating a first lipid fraction in a sample; obtaining a measurement of light scattering in the first lipid fraction; and calculating a particle count for the first lipid fraction that is a function of the measurement of light scattering.

Such a method may also comprise separating a second, third to $n^{th}$ lipid fraction in a sample; obtaining a measurement of light scattering for at least one of the fractions; and calculating a particle count at least one of the fractions, wherein the particle count is a function of the measurement of light scattering.

The additional lipoprotein fractions may be fractions based on density. For example, the first fraction and the additional fraction may be independently selected from the group consisting of: HDL, LpA, LDL, IDL, and VLDL. As explained herein, the approximately linear functions of light scattering to particle count may differ depending on the fraction being counted.

A more particular embodiment of the method comprises separating at least an HDL fraction, an LDL fraction, and a VLDL fraction in a sample; obtaining a measurement of the light scattering from at least one of the fractions; and calculating a particle count for each of the fractions from which a light scattering measurement was obtained, wherein the particle count is a function of the measurement of light scattering.

The method may further comprise separating additional fractions in addition to an HDL fraction, an LDL fraction, and a VLDL fraction in a sample; obtaining a measurement of the light scattering from at least one of the fractions; and calculating a particle count for each of the fractions from which a light scattering measurement was obtained, wherein the particle count is a function of the measurement of light scattering.

In one embodiment, the method comprises separating at least an HDL fraction, a lipoprotein A (LpA) fraction, an LDL fraction, and a VLDL fraction in a sample; obtaining a measurement of the light scattering from at least one of the fractions; and calculating a particle count for each of the fractions front which a light scattering measurement was obtained, wherein the particle count is a function of the measurement of light scattering.

In one embodiment, the method comprises separating at least an HDL fraction, a lipoprotein A (LpA) fraction, an LDL fraction, an intermediate density lipoprotein (IDL) fraction and a VLDL fraction in a sample; obtaining a measurement of the light scattering from at least one of the fractions; and calculating a particle count for each of the fractions from which a light scattering measurement was obtained, wherein the particle count is a function of the measurement of light scattering.

In one aspect of the foregoing methods, a particle count is obtained for the LDL fraction. In one aspect of the foregoing methods, a particle count is obtained for the LDL fraction and at least one additional fraction. In one aspect of the foregoing methods, a particle count is obtained for the VLDL fraction. In one aspect of the foregoing methods, a particle count is Obtained for the IDL fraction. In one aspect of the foregoing methods, a particle count is obtained for the LpA fraction.

In another embodiment of the method, only atherogenic lipoproteins are counted. Such an embodiment will comprise obtaining a measurement of light scattering from at least one atherogenic lipoprotein fraction and calculating a particle count for each of the atherogenic lipoprotein fractions from which a light scattering measurement was obtained, wherein the particle count is a function of the measurement of light scattering. The atherogenic lipoprotein may be selected from the group consisting of: LpA, LDL, IDL, and VLDL. In a specific embodiment the atherogenic lipoprotein is LDL. In another specific embodiment the atherogenic lipoprotein is LpA. Lipoprotein A is known to being strongly predictive of cardiovascular disease, yet there are very few methods by which LpA can be easily and accurately measured in serum samples.

The following is relevant to the methods described herein.

The subject may be any animal having serum lipoproteins to be measured. In the clinical setting the subject will often be a human patient, although it is conceivable that the subject will be a non-human animal in the veterinary setting. The subject may be human or non-human animal in the research setting. The animal in the research setting may be, for example, any commonly used model organism.

The lipid fraction from the subject will comprise a lipoprotein fraction, such as an HDL fraction, an LpA fraction, an LDL, fraction, an IDL, fraction, and/or a VLDL fraction. The lipid fraction may be substantially pure such that it will be sufficiently free from other components that could affect the photometric measurement that a quantitative value for the lipid fraction can be obtained. Non-interfering components that do not affect the photometric measurement may be present. The fraction will not be completely free of interfering components in every embodiment. For example, there may be some amount of another lipoprotein fraction present. In a specific example, when lipoprotein fractions are fractionated on the basis of density, there may be overlap between adjacent lipoprotein fractions; there may be LpA present in the HDL fraction and the LDL fraction, or there may be IDL present in the LDL fraction and the VLDL fraction.

In some embodiments of the method, the lipoprotein fraction consists essentially of serum components. In such embodiments the fraction contains no additional reagents, dyes, or other substances that may be added to facilitate measurement. This is possible in such embodiments because, unlike many other methods of quantifying lipoproteins, many embodiments of the photometric methods disclosed herein do not require the addition of reagents, dyes, fluorochromes, or the like. Any such artificially introduced substances that facilitate measurements are referred to herein as "analytical reagents." In some embodiments of the method the lipoprotein fraction contains no substantial amount of analytical reagents, such that any analytical reagents present are present in sufficiently low concentrations that they do not affect the measurements. In other embodiments the lipoprotein fraction contains no analytical reagent.

The particle count is calculated as a function of the photometric measurement. In some embodiments the function is approximately linear. In some embodiments the photometric measurement will be in the form of a curve, typically representing the relationship between run time and detector levels. Characteristics of such curves that are used to establish the photometric measurement include peak height and peak area. Peak area is calculated in a variety of ways, most often simply by multiplying the peak height by half of the distance from trough to trough (as if the peak were a triangle). Software is often provided with measuring devices that automatically computes peak area. In cases in which two peaks are not completely resolved, "deconvolution" transformations may be performed to determine a poorly resolved peak area; this involves taking the area of an aggregate peak and subtracting the contribution of one peak (generally the better resolved peak) to determine the area of the remaining peak.

Deconvolution is commonly used to resolve small peaks from larger adjacent peaks. In such cases often the smaller peak is only visible as a trough between two larger adjacent peaks, wherein the trough is not as deep as expected. The process comprises extrapolating the expected area under the trough between the larger peaks, subtracting the expected area of the trough from the actual area of the actual trough, wherein the difference in areas is the area under the smaller peak.

Examples of small lipoprotein peaks calculated by deconvolution are shown in FIGS. 8-11. The heavy black line shows actual light scattering values. The thinner lines show extrapolated peaks for each of the fractions (from left to right: HDL, LpA, LDL, IDL and VLDL). The shaded peak is the IDL peak, calculated by deconvolution of the LDL and VLDL peaks. The peak marked with horizontal hash lines is the LpA peak, calculated by deconvolution of the HDL and LDL peaks.

Light scattering has been discovered to effectively enumerate lipoprotein particles after only crude separation of lipoprotein fractions and without the use of additional reagents or dyes. In a specific embodiment the photometric measurement is light scattering. Light scattering may be measured over any detection arc, for example 360°, 180°; 90°, or 45°. In a specific embodiment light scattering is measured over a 90° detection arc.

The separation of the lipoprotein fraction may be accomplished by any means known in the art. The use of density-gradient centrifugation is a particularly useful approach to separating lipoprotein fractions from blood serum; it is simple, fast, inexpensive, and can be performed on numerous samples simultaneously. The density gradient may be created in a number of ways. For example, potassium bromide can be used to create a suitable gradient for lipoprotein separation. Potassium bromide may be used, for example, at a concentration of 1.21 g/mL. Other commonly used density gradient materials include cesium chloride, sucrose, and colloidal silica particles coated with polyvinylpyrrolidone (such as the product sold as Percoll®). Any density gradient solution known in the art to create the required density range may be used. Centrifugation will be performed in an appropriate vessel, such as a centrifuge tube. A variety of suitable centrifuge tubes are commercially available, for example from Beckman-Coulter, of Brea, Calif. In a specific embodiment separation is achieved using a single spin.

Light scattering can be measured by various means known in the art. In a particular embodiment, light scattering is measured using a laser light scattering detector. The detector may be a fixed-angle detector or a multi-angle detector. For a lipoprotein particle of a given type the amount of light scattering is approximately proportional to the number of particles per unit volume. Typically scattering is measured over a set arc, for example 360°, 180°, 90°, or 45°. In a specific embodiment light scattering is measured over a 90° detection arc. The particle count is an approximately linear function of light scattering, although the functions may differ depending on which lipoprotein fraction is being measured. The function can be determined by the calibration methods described below.

It is foreseeable that in some instances a linear relationship between particle count and light scattering for a given fraction will be linear only over a certain range of concentrations, and that above and below that certain range the relationship will not be linear. In such cases, when there is an indication that the particle count is outside of the range in which the relationship is linear, the sample may be either concentrated car diluted to obtain a sample with a particle count in the linear range. The calculation of the particle count will then be corrected for the dilution or concentration of the sample.

Some embodiments of the method comprise measuring the light scattering of more than one lipoprotein fraction, such that the light scattering of the highest density fraction to be measured is measured before the others. In some such embodiments the light scattering of each fraction is measured in order of descending density. That is to say that the light scattering of the fractions would be measured in the following order, with the understanding that not all of the listed fractions need be measured: HDL, LpA, LDL, IDL, VLDL. As an illustrative example, if only LDL and VLDL are to be measured, LDL would be measured first, followed by VLDL. In a particular embodiment, the sample is prepared by density-gradient centrifugation, and the sample is drained from the bottom such that the highest density fractions are collected first and sent to a light scattering counter.

Another embodiment of the method comprises measuring the particle count of a lipoprotein fraction of a sample in any of the apparatuses disclosed below.

C. Apparatus for Quantifying Lipoproteins

An apparatus is provided for quantifying lipoprotein particles in a plurality of serum lipid fractions. The apparatus generally functions by collecting lipoprotein fractions from a sample one fraction at a time and transporting each fraction to a light scattering counter. The counter then measures the scattered light, which can be used to calculate the particle count for the fraction.

A general embodiment of the apparatus comprises: a liquid conduit positioned to collect a sample from a sample vessel; and a light scattering counter positioned to receive the sample from the conduit. In one embodiment, the sample is collected from the bottom of the sample vessel.

The sample vessel may be any sample container known in the art. In some embodiments of the apparatus the sample vessel is a centrifuge tube. The use of a centrifuge tube has the advantage of using the same vessel for separation and for sampling. The centrifuge tube may have a bottom surface that is easily pierced by a sampler. In such embodiments a septum may be present on the bottom surface or the bottom surface may be a relatively thin structure.

The liquid conduit may be any structure suitable for conveying the liquid in the sample to the light scattering counter. Examples of such structures include pipes, tubes, channels, hoses, or any other conduit suitable for carrying liquid as known in the art. In a specific embodiment, the conduit is 8 mm (internal diameter) Teflon tubing. In one embodiment, the liquid conduit will be positioned to collect the sample from the bottom of the vessel. This allows the collection of vertically stratified layers, as will occur when lipoprotein fractions are separated by density-gradient centrifugation. Some embodiments of the liquid conduit comprise a sampler connected to the conduit to facilitate collection of the sample. In a specific embodiment the liquid conduit is connected to a sampling needle. The sampling needle may be positioned to penetrate the sample vessel to as to allow the liquid from the sample vessel to flow through the needle into the conduit. The diameter of the tubing may be varied to obtain a suitable flow rate of sample; the length of the tubing and the relative elevation of the sample vessel and the counter will also affect the flow rate, as is understood by those skilled in the art. All of these factors may be varied as needed.

The light scattering counter may be any suitable instrument, for example a laser light scattering counter. It may be configured to measure scattered light across any arc, as described above. The counter may comprise a flow cell, in which case the conduit may be connected to the flow cell so as to allow the liquid from the sample vessel to enter the flow cell wherein its light scattering properties will be measured.

The apparatus may further comprise a pump configured to pump the sample through the conduit to the counter. Various types of pumps may be used. In a specific embodiment the pump is a piston pump, which allows good control over the flow rate of the liquid.

The apparatus may comprise a sensor proximate to the conduit, wherein the sensor measures a fluid property within the conduit, and wherein said fluid property significantly differs in air and in liquid. The sensor is thus capable of distinguishing air from liquid in the conduit. Properties that can be used to distinguish air from liquid are well known in the art, and include thermal conductivity, electrical resistance, optical absorbance, and optical diffraction. Sensors capable of measuring these properties are well known in the art.

If air is detected in the conduit it might indicate that an entire sample has been taken, and that the sample vessel is now empty. In one embodiment, the sensor transmits a signal to indicate the presence of air in the conduit. In one embodiment, the sensor may send a signal to the pump to cease drawing fluid from the sample vessel when air is detected in the conduit. In some embodiments of the apparatus the sensor is connected to transmit a signal to a valve positioned on the conduit. In such embodiments the sensor may send a signal to close the valve when air is detected in the conduit.

The apparatus may further comprise a data logger connected to the counter. The data logger may record the data either digitally on graphically (i.e., on a paper printout). In embodiments in which the data are recorded on computer-readable media, the data may be further processed by a computing device. In some such embodiments the particle count for the lipoprotein fractions is computed by the computing device without direct human intervention. The resulting particle count may then be displayed or recorded. The term "computer-readable media" as used herein refers to a medium of storing information that is configured to be read by a machine. Such media include magnetic media, optical media, and paper media (punch cards, paper tape, etc.). Printed writing in a human language, if not intended or configured to be read by a machine, is not considered a computer-readable medium. In no case shall a human mind be construed as "computer-readable format."

The apparatus may also comprise a filter positioned on the conduit between the sample vessel and the counter. The filter functions to remove additional interfering particles. The pore size of the filter must be greater than the diameter of the lipoprotein to be counted. Ideally the pore size of the filter will be only slightly greater than the diameter of the lipoprotein to be counted, although it is to be understood that most classes of lipoprotein show a range of sizes. Filters with 100 nm pore size are quite suitable; they are readily available commercially and remove a significant amount of interfering serum components without removing lipoproteins. All lipoproteins, except chylomicrons, are less than 100 nm in diameter. Pre-filtration may also be provided to remove larger particles to enhance the lifespan of a fine filter (such as the 100 nm fine filter described above); for example, a 2 µm pore-size filter will effectively remove larger particles.

The apparatus may comprise a reservoir of a cleaning fluid, such that the components of the apparatus may be flushed between samples. The cleaning fluid may be as simple as saline solution, de-ionized water, saline made from filtered de-ionized water, or any of these with the addition of detergents and surfactants. A specific embodiment of the cleaning fluid is a 40% v/v solution of Cleanz™ in water. The reservoir may be connected to a cleaning conduit that joins the main conduit between the valve and counter (downstream from the sensor and the sample vessel). The reservoir may be positioned above the components to be flushed to impart sufficient hydraulic head to cause the cleaning fluid to flow through the components under the force of gravity. A pump may be positioned to impart additional hydraulic head pressure to the cleaning fluid. While the valve is open the fluid will flush the end of the conduit positioned to collect the sample. While the valve is closed the fluid will flow through the conduit to the counter.

In one embodiment, the apparatus may be in communication with a control unit. The control unit is in communication with the various components of the apparatus and may receive input from such components and/or control the operation of such components. For example, the control unit may comprise the data logger, which as described above, receives the measurements of light scattering obtained from the light scattering counter. The control unit may contain executable programs to carry out functions associated with the methods described herein. For example, the control unit may comprise an executable file use to deconvolute the data generated. Furthermore, the control unit may comprise an executable file that generates a particle number from the light scattering data measured. In one aspect, the executable file is or contains an algorithm described herein. In one embodiment, the control unit is a general purpose computer. The general purpose computer may be programmed to carry out the functions described.

In another general embodiment, the apparatus comprises means for containing a liquid sample having vertically stratified fractions; means for conveying the lowest stratified fraction from the containing means; and means for counting particles configured to receive the lowest stratified fraction from the containing means by way of the conveying means. In some embodiments of the apparatus the means for counter particles are means for measuring light scattering. The apparatus may comprise means for flushing configured to flush the means for conveying and to flush the means for counting particles. The apparatus may also comprise means for sensing air within the conveying means.

Turning now to FIG. 1, an embodiment of the apparatus is presented comprising a sampling needle configured to puncture the bottom of a sample vessel; a tube having a first end and a second end, the first end connected to the sampling needle to receive a liquid sample from the needle; a light scattering counter connected to the second end of the tube and configured to measure light scattering in the sample when conveyed through the tube; an optical sensor positioned to measure the optical absorbance in the tube and capable of distinguishing air from liquid; a primary pump configured to pump the sample from the needle through the tube to the counter; a solenoid valve downstream of the sensor and connected to the sensor to receive an electrical signal causing the valve to close when air is detected by the sensor; and a flush reservoir connected to the tube.

D. Method of Calibration

Measurements of particle count of atherogenic lipoproteins may be calibrated by comparing the results of other methods of counting atherogenic lipoprotein particles to photometric data. Apolipoprotein B (apoB) is particularly useful in this regard, as there is only one molecule of apoB present in a given particle of LpA, LDL, IDL, or VLDL (collectively referred to as "atherogenic lipoproteins"). A method for calibrating the measurement of a particle count of an atherogenic lipoprotein is provided, the method comprising: obtaining a photometric measurement of an atherogenic lipoprotein from a calibration sample; measuring the molar concentration of apoB in the atherogenic lipoprotein fraction of the calibration sample; and calculating a regression between the photometric measurement and the molar concentration of apoB. The atherogenic lipoprotein may be selected from the group consisting of: LpA, IDL, LDL, and VLDL. The photometric measurement may be any disclosed above as suitable for determining the particle count of lipoproteins, including the measurement of light scattering. The regression may be an approximately linear regression, as would be expected between a measurement of light scattering and the particle count of a lipoprotein.

The molar concentration of apoB may be measured by various means known in the art. For example, commercially available immunoassays can be used to quickly and accurately measure the concentration of apoB in fractions containing atherogenic lipoproteins from a sample. Such immunoassays may take any form in the art, including fluorescent, enzymatic and magnetic assays. One suitable assay is the Architect® system, available from Abbott Labs.

In many cases more than one calibration measurement will be necessary. Thus, the method may comprise obtaining a photometric measurement of the atherogenic lipoprotein from a second calibration sample; measuring the molar concentration of apoB in the second calibration sample; and calculating a regression based on the photometric measurement in the calibration sample, the molar concentration of apoB in the calibration sample, the photometric measurement in the second calibration sample, and the molar concentration of apoB in the second calibration sample. Additional measurements may be made as discussed above, as necessary to establish a sound regression.

E. Examples

1. Sample Collection and Separation

A fasting blood sample is collected from the subject. Such a sample is collected as is known in the art, such as in a serum separator tube (SST) or plain red top serum tube. Serum is separated according to standard procedure and filtered to remove any clots, fibrin and any large interfering particles.

In one embodiment, samples are subject to density gradient centrifugation to separate lipid components. Density gradients were prepared using either manual pipette and dispensing devices or an automated liquid handler such as the Tecan Genesis™). Multiple serum samples may be processed at one time. In one embodiment, a batch consisting of 16 serum samples is simultaneously prepared using an automated liquid handler. The following steps were used in the following examples:
1. Pipette 50 µL serum and mix with 1950 µL of 1.21 g/mL KBr solution.
2. Pipette 3.56 mL of 1.006 g/mL, saline solution into a 5 mL Beckman centrifuge tube.
3. Slowly underlay 1.4256 ml of above prepared serum: KBr mixture to prepare a two density layer gradient.

Once the density gradient was prepared, all 16 centrifuge tubes with density gradients were placed in a Beckman Vertical Rotor (VTi 65) and centrifuged at 65,000 rpm for 47 minutes (including acceleration and deceleration) using a Beckman Coulter Optima XL 100 ultracentrifuge.

2. Apparatus

Particle concentration (in terms of moles of particles per unit volume) of separated lipoprotein classes and subclasses in the centrifugate were measured by using a working embodiment of the apparatus (referred to in this example simply as "the apparatus"). The apparatus is be an automated continuous flow through analysis system consisting of an automated specimen rack moving system, a tube piercing needle that can be automatically raised to pierce the tube, an end of sample drain detector, a sample valve that closes and opens automatically as programmed to facilitate the flow of sample from centrifuge tube, a piston pump to drain the sample from the centrifuge tube at a predetermined flow rate, a programmed pneumatic valve that allows the flow of baseline solution when sample is not flowing, a narrow bore (0.8 mm internal diameter) Teflon® tubing of a predetermined length (25 inches) that connects the pump to the multi-angle laser light scattering flow through detector (Wyatt Technology, Santa Barbara, Calif.) which outputs a light scattering signal proportional to the concentration of lipoprotein particles flowing through, an in line filter containing a 100 nm pore-size filter to remove interfering blood components placed between pump and detector, and software (ASTRA) that continuously collects the digital signal from the detector as sample flows through the detector. The sample is run at a flow rate of 3 mL per minute, using 25 inches of 0.8 mm Teflon™ tubing (resulting in a drain time of 1 minute 45 seconds). As the separated lipoprotein particles flow through the flow cell of the detector a laser impinges on the particles. As a result, they scatter light at various angles. The Wyatt instrument (DAWN HELEOS II) has 18 detectors (photodiodes) placed around the flow cell which collect signal from scattered light at their respective angles. The intensity of light is proportional to the type and number of lipoprotein particles flowing through. The signal is measured coming out of the detector placed at 90°. The method does not require any reagent, as it depends upon the physical phenomenon of light scattering. Such embodiments of the method simplify the instrumentation as well as reduce the cost of analysis.

3. Analysis

As the separated lipoprotein particles (all lipoprotein particles are separated based upon their density during ultracentrifugation with high density lipoprotein separating at the bottom of the centrifuge tube low density lipoprotein in the middle and very low density lipoprotein at the top) pass through the detector continuously during the draining of contents of centrifuge tube a continuous signal is obtained which consists of light scattering intensity peaks that correspond to respective lipoprotein classes and subclasses as shown in FIGS. 2-5. The area of each peak is proportional to the respective number of particles of that lipoprotein per unit volume. Since the single vertical spin density gradient ultracentrifugation does not provide fully resolved (base line separated) peaks, software deconvolutes the main continuous signal output curve into its component peaks corresponding to different lipoprotein peaks. Examples of deconvoluted profiles are shown in FIGS. 8-11, as more fully explained above. The resulting profile has three major peaks for fractions of decreasing density going from left to right (as the time variable increases) corresponding to the HDL, LDL, and VLDL; and two minor peaks corresponding to LpA and IDL.

4. Instrument Calibration

Figure 12:
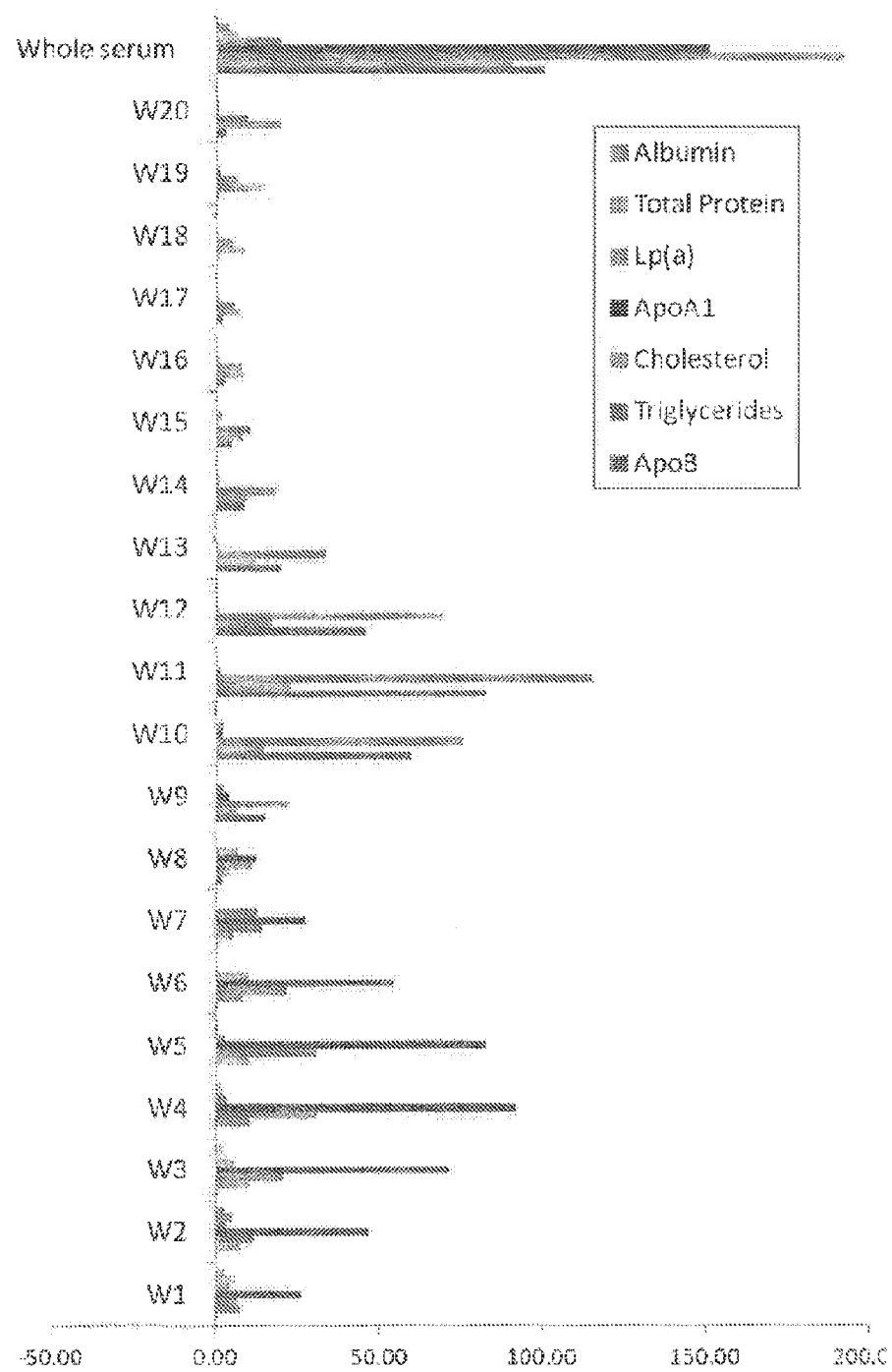
FIG. 12: An illustration of potential interfering serum components in density fractions of serum.

In order to convert the area under each peak to a respective particle count, the area for each lipoprotein fraction will be calibrated separately. Lipoproteins are heterogeneous in terms of their physical characteristics (such as size and shape) and their chemical characteristics (such as composition), and thus the light scattering from each class of lipoprotein is may differ. The HDL peak may contain signal interference to due to various other blood components such as serum albumin and other non-lipoprotein related proteins (see FIG. 12). Quantification of an analyte usually utilizes a known standard (i.e., a substance with a known concentration of the analyte) to calibrate the system. Currently there are no commercially available lipoprotein standards with known particle counts (number per volume or nM) nor are there commonly accepted reference methods. In order to overcome this problem, apoB was used as a calibrator, due to the fact that each atherogenic lipoprotein particle (LDL, VLDL, IDL, Lp(a) and their subclasses) contains only one molecule of apoB and thus if apoB concentration is known in each atherogenic class of lipoprotein in a given serum the concentration of particles is known. This principle was used to calibrate the system for counting LDL particles. This will be achieved for other fractions by separating the lipoproteins into fractions using the ultracentrifugation procedure described above, collecting a fixed number of equal volume fractions in test tubes, and subsequently analyzing apoB in each fraction using a standardized immunoassay method. To this end the Abbott Architect C8000 instrument was used, with an immunoassay available from Abbott Labs which has been standardized using WHO-International Reference Material (SP3-07) by participating in the Apolipoprotein Standardization Program by Northwest Lipid Metabolism and Diabetes Research Laboratories, University of Washington, Seattle.

A serum volume appropriately adjusted to 1.21 g/mL was be used to achieve immunoassay-measurable concentrations of apoB (if present) in the LDL fractions. Once the apoB concentrations are established in each fraction collected, the apoB concentration of the peak corresponding to each class of atherogenic lipoprotein will be calculated by adding the apoB concentration of each sub-fraction that constitutes that peak. Each peak area can then be calibrated with its corresponding apoB concentration. A calibration curve can be prepared for each atherogenic lipoprotein class by repeating the above procedure with several serum samples with increasing amounts of apoB. The slope and intercept of this calibration curve can be used to obtain apoB concentration of atherogenic lipoprotein classes under testing for an unknown serum sample. The apoB concentration of peak for the atherogenic class of lipoprotein thus obtained can be converted to lipoprotein particle concentration using the Avogadro constant ($6.022 \times 10^{23}$) and molecular weight of the apoB molecule (550 kDa) since each atherogenic particle contains only one molecule of apoB (one mole of any substance contains $6.022 \times 10^{23}$ particles).

The calibration curve for LDL was determined as described in the previous paragraph using 6 serum samples with increasing apoB concentrations.

Figure 6:
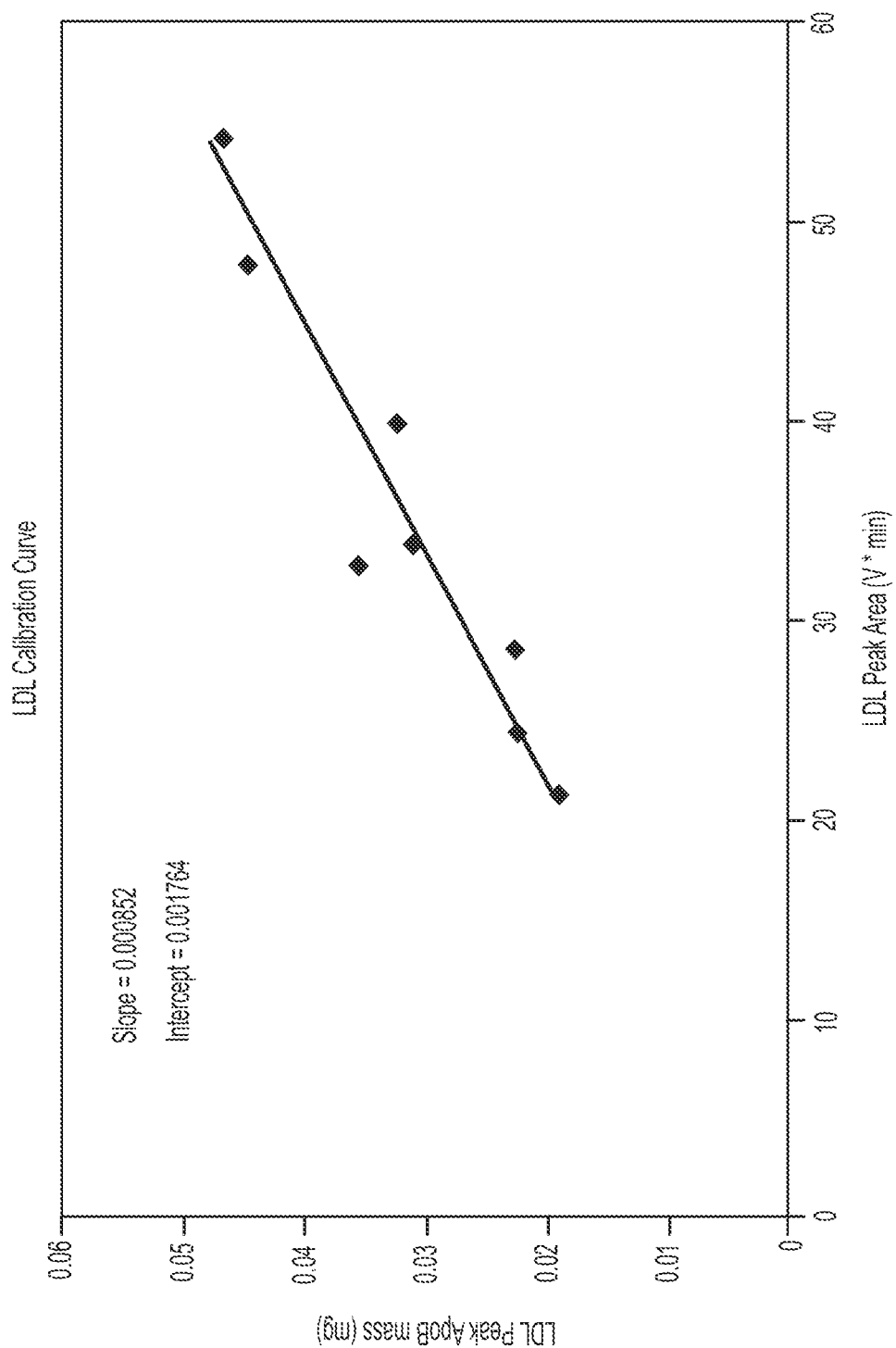
FIG. 6: A calibration curve showing the relationship between peak area in the LDL fraction obtained by measuring light scattering (in units of volt-minutes) and mass of apoB in a 37.3 μL serum sample.

FIG. 6 illustrates an actual calibration curve showing the relationship between the peak area for the LDL fraction in a sample and the mass of apoB in the LDL fraction of the sample. The samples in question were 37.3 µL human serum samples. The peak area represents the volt-minutes under the peak obtained using a light scattering detector after the LDL fraction had been separated from the other serum components by density-gradient centrifugation. ApoB mass in the LDL fraction was determined by commercial immunoassay. A least-squares regression was calculated using the eight data points shown. The relationship between the peak area for the LDL fraction in a sample and the mass of apoB in the LDL fraction of the sample was calculated to be:

$$y = 1.764 \cdot 10^{-3} \text{ mg} + (8.52 \cdot 10^{-4} \text{ mg } V^{-1} \text{ min}^{-1})x \qquad \text{Equation 1}$$

y=mass of apoB in the LDL peak (mg)
x=LDL peak area (V·min)

Based on the calculated apoB mass and on the known sample volume, one can then calculate the mass density of apoB in the sample. The molarity of apoB can be calculated based on the mass density apoB and the known molecular weight of apoB ($5.5 \times 10^5$ g mol$^{-1}$). Because each particle of LDL contains exactly one apoB molecule, the molarity of LDL particles (wherein the mole is used as a unit of quantity to be applied to LDL particles) will be exactly the same as the molarity of apoB.

Based on eight samples the regression provides a correlation coefficient of 0.96.

Figure 7:
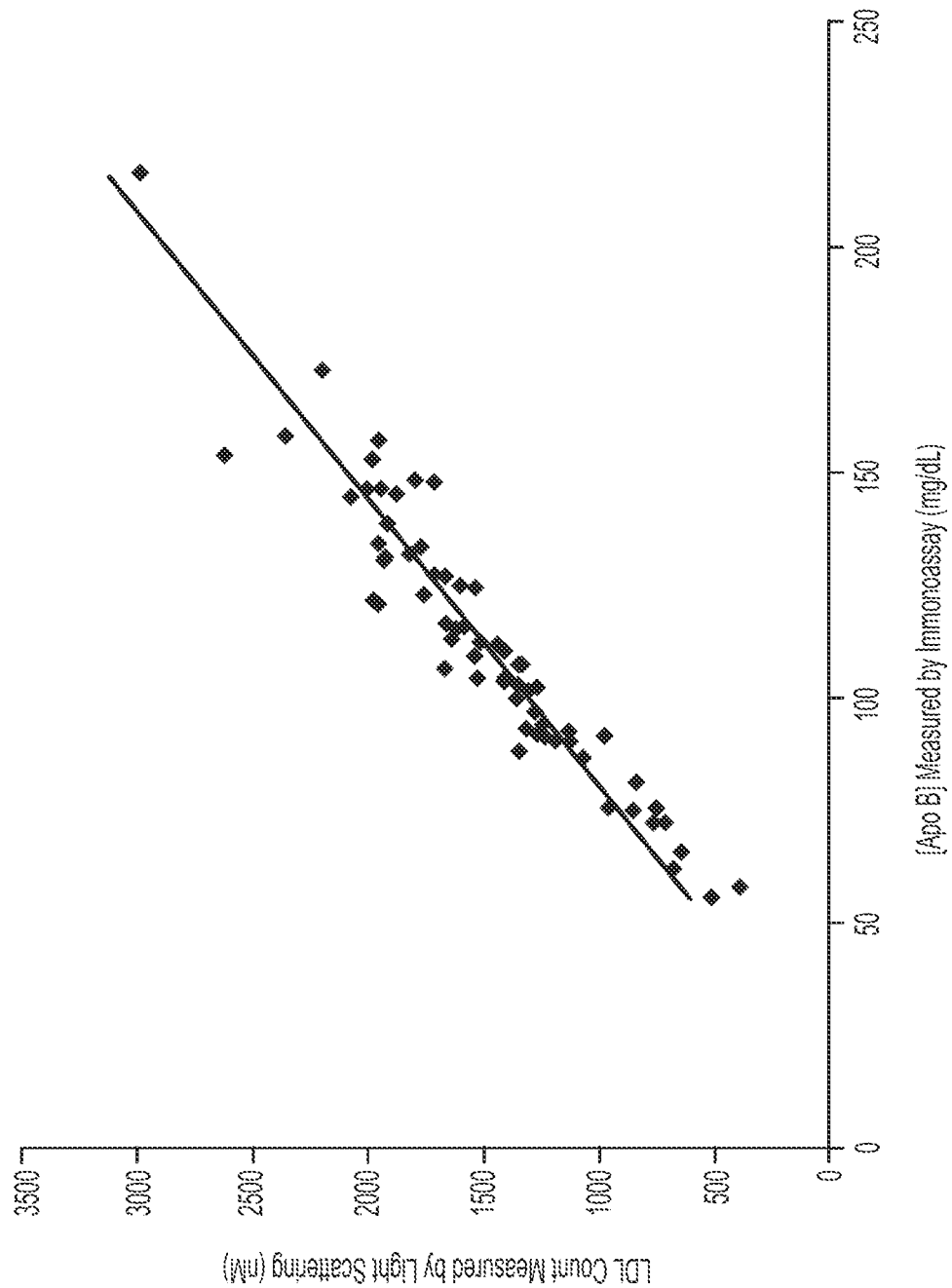
FIG. 7: A graph illustrating the agreement between apoB concentration as measured by immunological techniques (horizontal axis) and LDL particle count as measured by light scattering.
Figure 8:
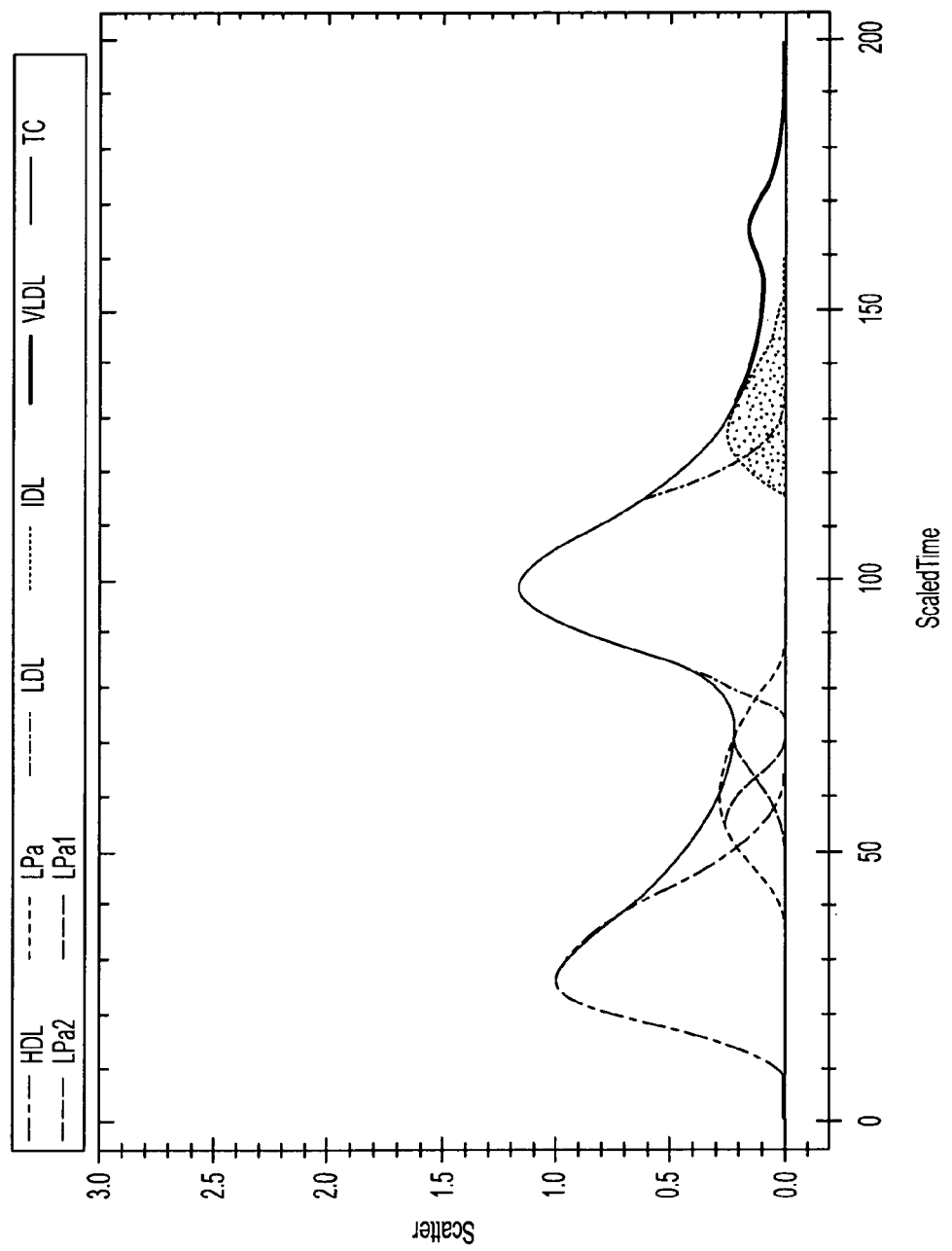
FIG. 8: A de-convoluted normal lipid profile.
Figure 9:
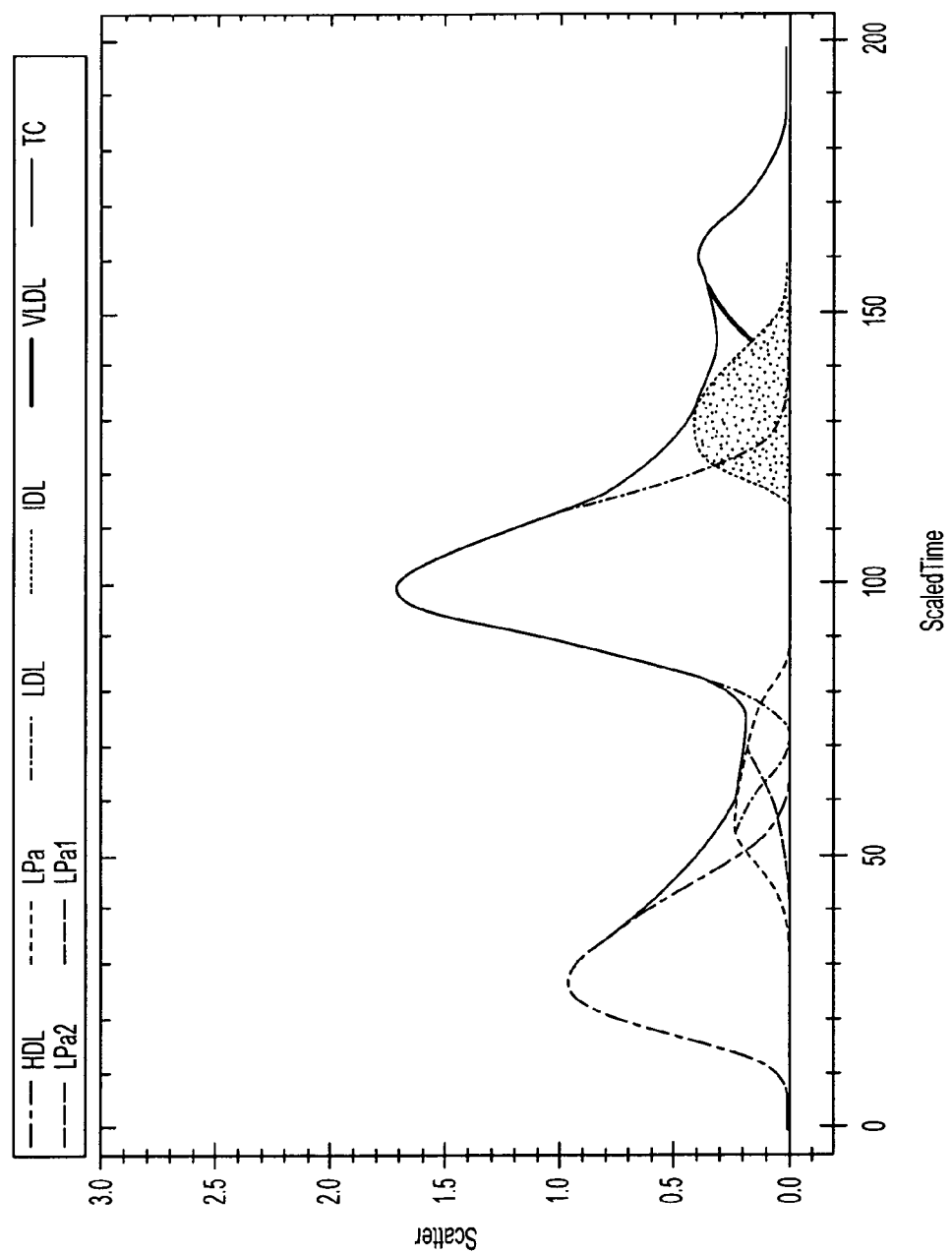
FIG. 9: A de-convoluted high-LDL lipid profile.
Figure 10:
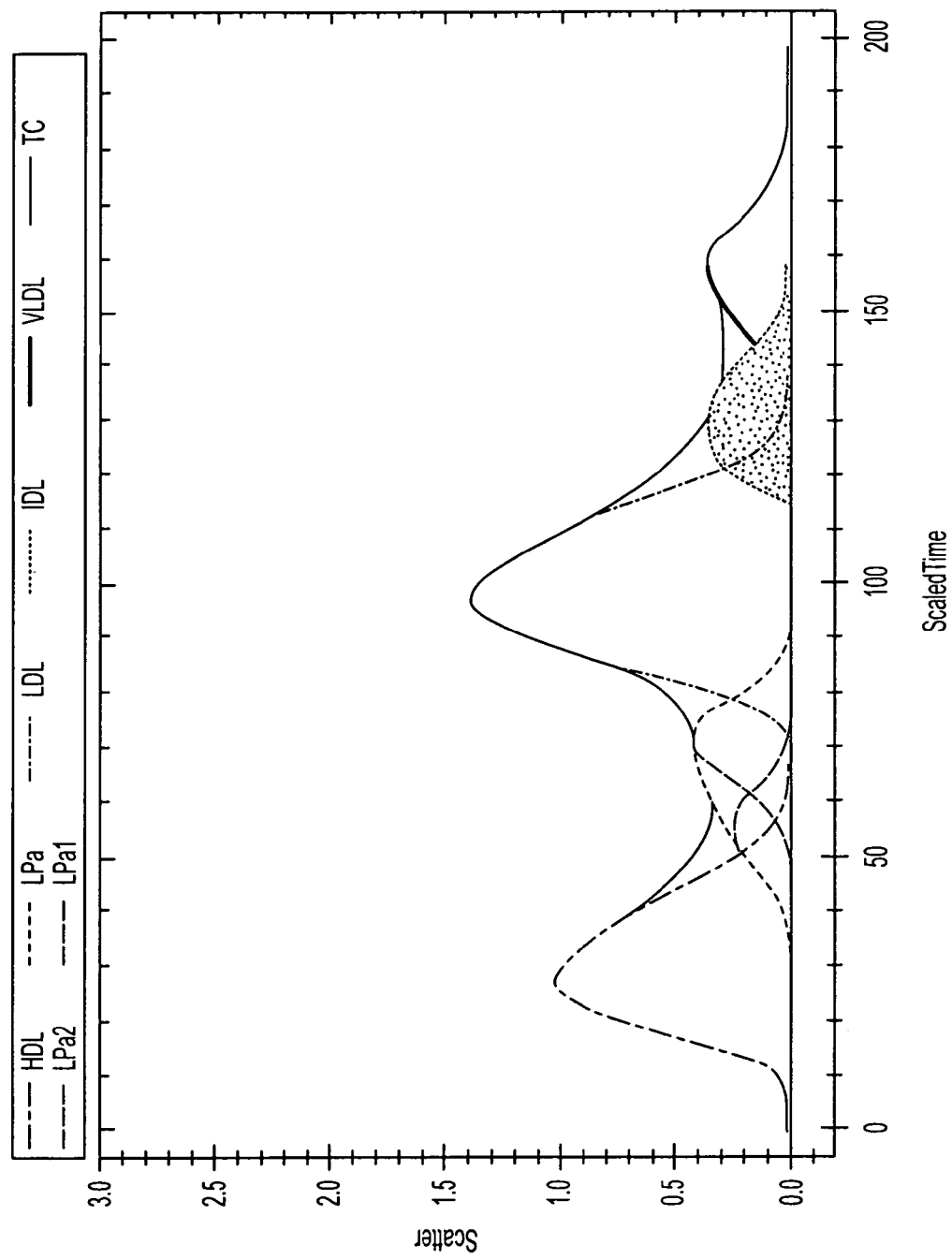
FIG. 10: A de-convoluted high-LpA lipid profile.
Figure 11:
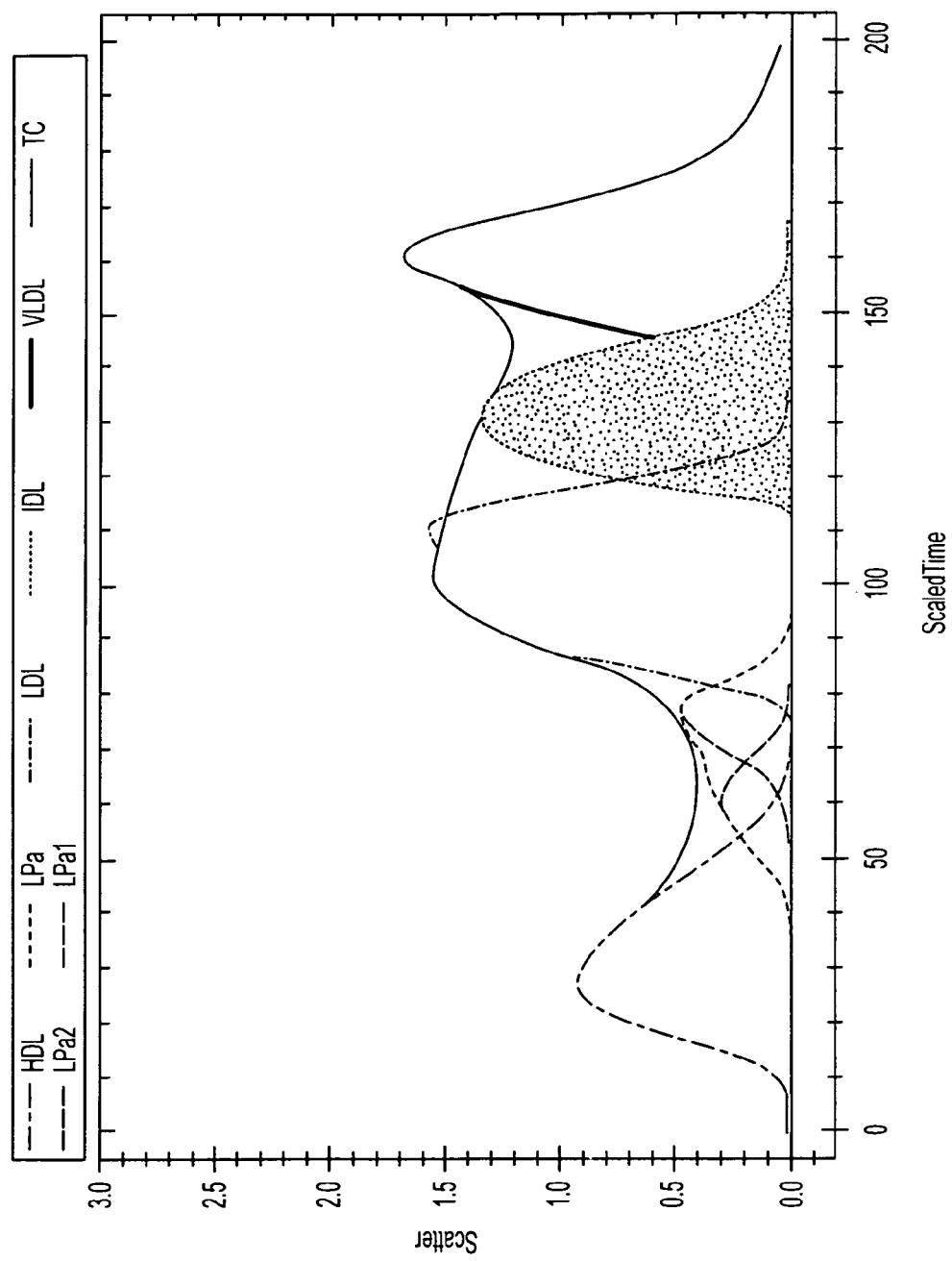
FIG. 11: A de-convoluted high-IDL lipid profile.

The regression was then tested for robustness using 64 human serum samples. FIG. 7 illustrates the relationship between the LDL particle count calculated from scattered light using the regression presented above (Equation 1) and the mass density of apoB as determined by commercial immunoassay. Each sample was separated into fractions using density gradient centrifugation. The mass density of apoB was measured in the serum by commercial immunoassay. The LDL particle count was measured in the LDL fraction by light scattering; the peak area provided by the scatter counter was transformed according to Equation 1 to calculate the LDL particle count, which was in turn used to calculate LDL particle count per unit volume by dividing the total particle count by the volume. The LDL peak area was subjected to deconvolution to resolve the LDL peak from any interfering peaks.

The results of the two methods were closely correlated. The best fit least-squares regression obtained had a calculated correlation coefficient of 0.953. This leads to the conclusion that light scattering is as reliable as are immunoassays for enumerating LDL particles.

Baseline

Between the draining of two samples and prior to starting analysis a stable and constant baseline should be achieved for quantification. Several different solutions are suitable, including water, saline, and various concentrations of Beckman's Cleanz™ solution. A stable and constant baseline was achieved with a solution of 40% Cleanz v/v in water.

Blank Spin

In order to assess interference due to solvents (KBr, saline, water, Cleanz™) and undissolved particles, a "blank" containing no serum (serum substituted with saline solution) was centrifuged and subjected to the lipoprotein counting protocol as described above. The blank profiles suggested a small drop in signal by KBr used for gradient preparation which was proportional to KBr concentration. Thus measurements from a blank run from the test sample were subtracted from the light scattering measurements for the lipoprotein fractions to correct. This process is embedded in the deconvolution algorithm.

Controls

To monitor the stability of the signal from day to day three pooled serum samples with increasing LDL-R particle counts (obtained from Solomon Park Research Laboratories, Seattle, Wash.) were run daily.

Precision

The precision of LDL particle counts was determined by preparing two pools of samples with normal and abnormal levels of LDL and performing the test on both pools 32 times per day for 5 days. Two human serum sample pools (normal and high LDL concentrations) were prepared by mixing several samples with similar LDL cholesterol values. Light scattering was measured in lipoprotein fractions that had been separated by density-gradient centrifugation on 32 replicates of each pool each day for 5 days. Within-day precision was calculated based on 32 aliquots of each pool and total precision (all 5 days combined) is based on 160 replicates of each pool. Coefficients of variation were calculated for each atherogenic fraction based on each day's measurements and based on the variation in measurements from day to day. The results are tabulated below:

| Lipoprotein Fraction | Coefficient of Variation on a Given Day | Coefficient of Variation Between Days |
|---|---|---|
| LpA | 1.77-4.57% | 4.13% |
| LDL | 1.28-2.16% | 1.79% |
| IDL | 1.73-6.00% | 4.68% |
| VLDL | 2.90-5.63% | 5.29% |

The results indicate a high degree of precision for the embodiment of the method in question.

Exemplary Results

Figure 2:
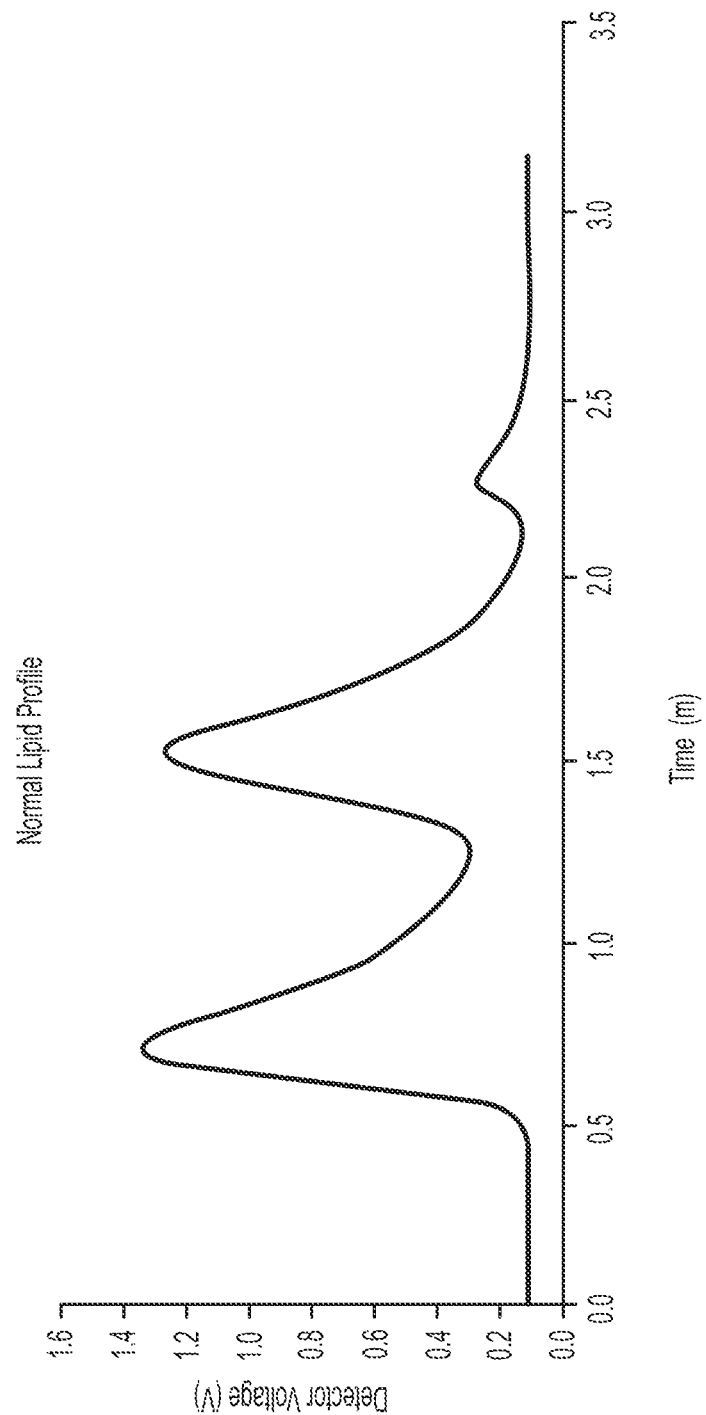
FIG. 2: A normal lipoprotein profile produced by an embodiment of the method using an embodiment of the apparatus.
Figure 3:
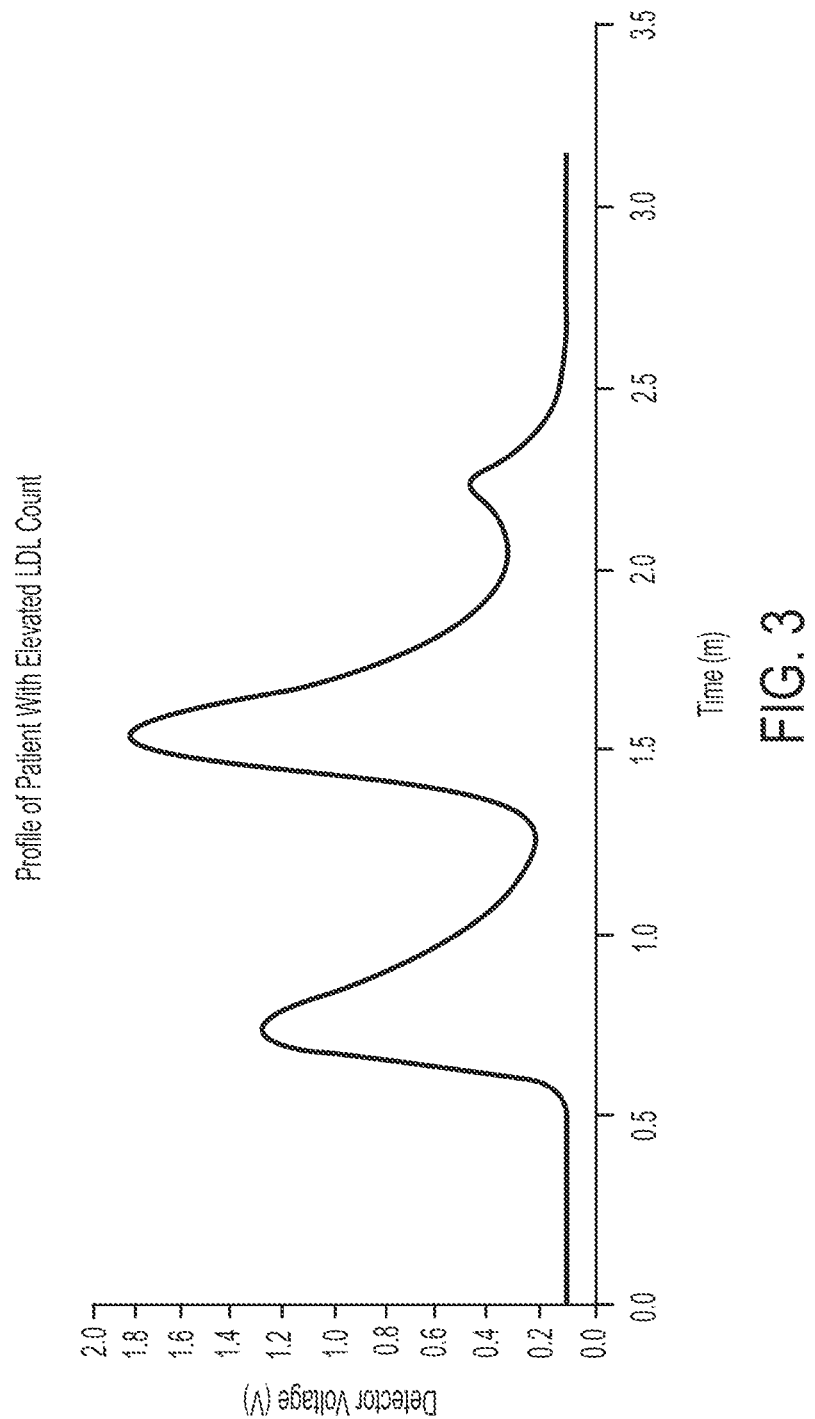
FIG. 3: A high-LDL lipoprotein profile produced by the same embodiment of the method and apparatus as in FIG. 2.
Figure 4:
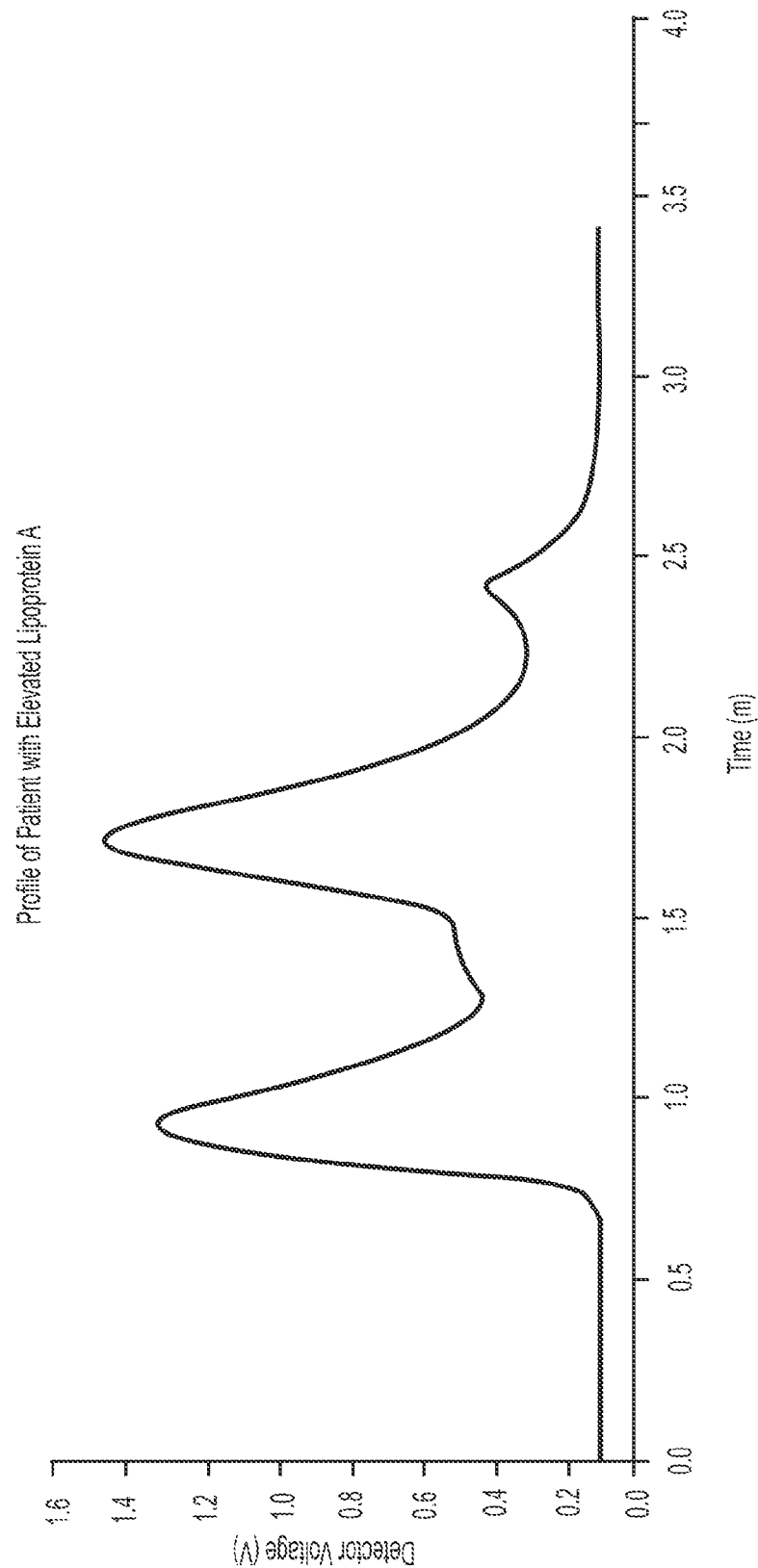
FIG. 4: A high-LpA lipoprotein profile produced by the same embodiment of the method and apparatus as in FIG. 2.
Figure 5:
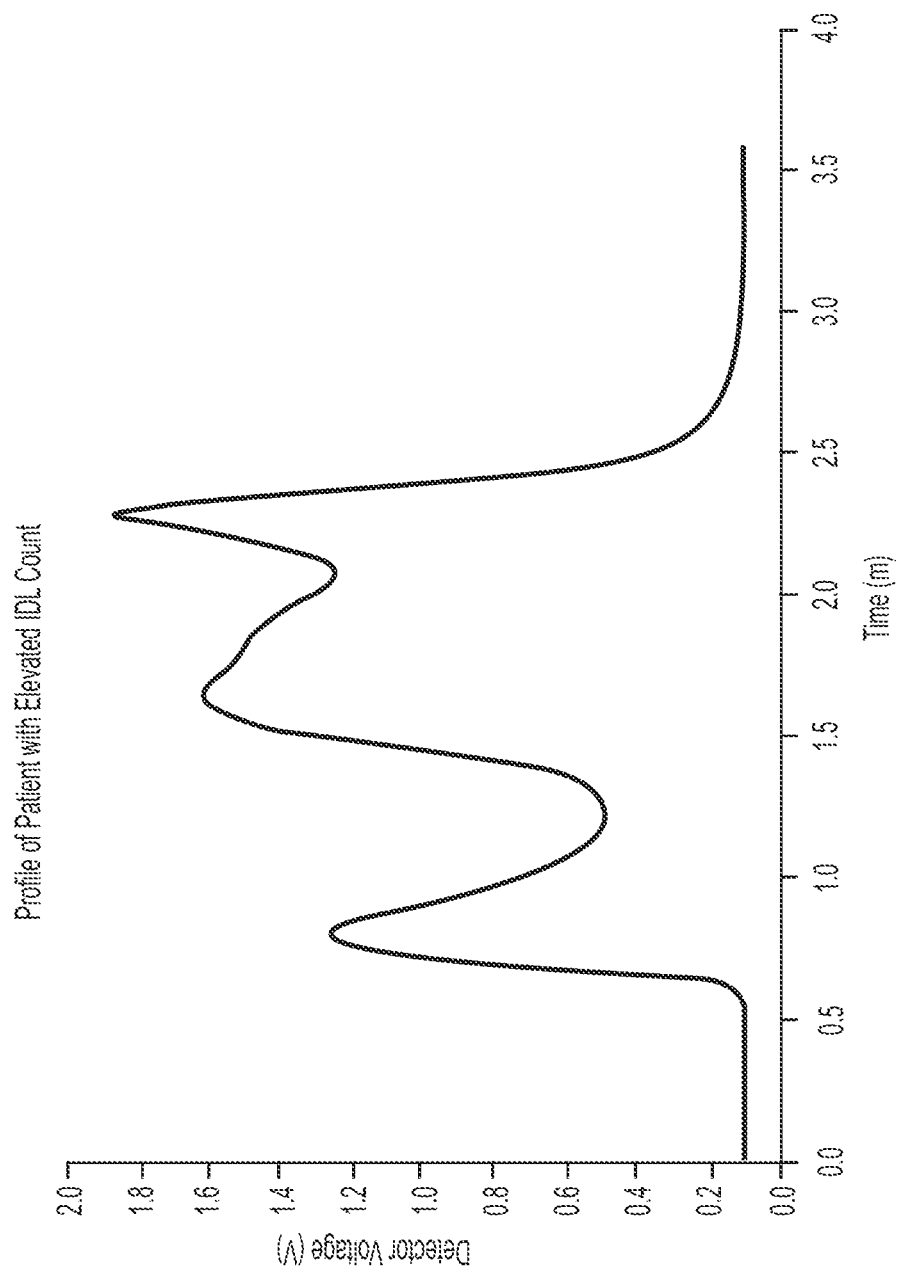
FIG. 5: A high-IDL lipoprotein profile produced by the same embodiment of the method and apparatus as in FIG. 2.

FIGS. 2-5 show the results of sample analysis using embodiments of the method and apparatus. FIG. 2 shows a normal lipid profile, showing three well-resolved peaks for the HDL, LDL, and VLDL fractions. FIG. 3 shows a high-LDL lipid profile, also showing three well-resolved peaks. FIG. 4 shows a high-LpA lipid profile, in which the LpA peak falls between the HDL peak and LDL peak; as can be seen the LpA peak is quite visible, but not completely resolved from the adjacent peaks. FIG. 5 shows a high-IDL lipid profile, in which a pronounced IDL peak falls between the LDL peak and VLDL peak.

F. Conclusions

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. It is to be understood that any given elements of the disclosed embodiments may be embodied in a single structure, a single step, a single substance, or the like. Similarly, a given element of the disclosed embodiment may be embodied in multiple structures, steps, substances, or the like. Any section headings herein are provided only for consistency with the suggestions of 37 C.F.R. §1.77 or otherwise to provide organizational queues. These headings shall not limit or characterize the disclosure set forth herein.

What is claimed:

1. A method of measuring lipoprotein particle concentration in a sample from a subject, the method comprising: (a) separating at least an HDL fraction, an LDL, fraction, and a VLDL fraction in a sample by centrifugation; (b) obtaining a measurement of the light scattering from the LDL fraction; (c) determining an apolipoprotein B concentration in the LDL fraction and (d) transforming the measurement of the light scattering from the LDL fraction to an LDL particle concentration.

2. The method of claim 1, wherein the transforming of step (d) is accomplished according to an LDL specific algorithm.

3. The method of claim 2 further comprising separating at least an HDL fraction, a lipoprotein A (LpA) fraction an LDL fraction, an IDL fraction and a VLDL fraction in a sample.

4. The method of claim 3, wherein the sample is contained in a tube and the tube is sampled from the bottom so as to collect the fractions in descending order of density.

5. The method of claim 1, wherein the sample is contained in a tube and the tube is sampled from the bottom so as to collect the fractions in descending order of density.

6. The method of claim 1, further comprising: (d) obtaining a measurement of the light scattering from the HDL fraction; and (e) obtaining a measurement of the light scattering from the VLDL fraction; wherein the steps of obtaining measurements of the light scattering of the HDL, LDL, and VLDL fractions are performed in order of descending density.

7. The method of claim 1, wherein the sample is a blood sample, further comprising separating at least an HDL fraction, a lipoprotein A (LpA) fraction, an LDL fraction, an IDL fraction, and a VLDL fraction in the sample; and transporting each fraction to a light scattering counter in order of descending density.

8. A method of measuring lipoprotein particle concentration in a sample from a subject, the method comprising: (a) separating at least an HDL fraction, an LDL, fraction, and a VLDL fraction in a sample using centrifugation; (b) obtaining a measurement of the light scattering from the LDL fraction; and (c) transforming the measurement of the light scattering from the LDL fraction to an LDL particle concentration using an LDL specific algorithm, wherein the algorithm is $y=1.764\times10^{-3}$ mg$+(8.52\times10^{-4}$ mg V$^{-1}$ min$^{-1})$x, where y is the mass of apolipoprotein B in mg and x is the LDL peak area in V(min).

9. The method of claim 2, wherein the LDL specific algorithm is $y=1.764\times10^{-3}$ mg$+(8.52\times10^{-4}$ mg V$^{-1}$ min$^{-1})$x, where y is the mass of apolipoprotein B in mg and x is the LDL peak area in V(min).

* * * * *